United States Patent [19]
Nakanishi et al.

[11] Patent Number: 5,133,705
[45] Date of Patent: Jul. 28, 1992

[54] SANITARY NAPKIN

[75] Inventors: Hirofumi Nakanishi, Ichikai; Hiromi Baba; Akira Sakurai, both of Utsunomiya, all of Japan

[73] Assignee: Kao Corporation, Tokyo, Japan

[21] Appl. No.: 704,229

[22] Filed: May 22, 1991

[30] Foreign Application Priority Data

Jun. 7, 1990 [JP] Japan ................................. 2-149382
Sep. 28, 1990 [JP] Japan ................................. 2-260076

[51] Int. Cl.$^5$ ............................................ A61F 13/16
[52] U.S. Cl. ................................. 604/387; 604/389
[58] Field of Search ........................ 604/387, 389, 390

[56] References Cited

U.S. PATENT DOCUMENTS

| 3,900,320 | 2/1975 | McCoy ................................. 604/389 |
| 4,084,592 | 4/1978 | Tritsch ................................ 604/390 |
| 4,168,196 | 9/1979 | Nemeth ............................... 604/390 |
| 4,177,812 | 12/1979 | Brown et al. ...................... 604/390 |
| 4,589,876 | 5/1986 | Van Tilburg . | |
| 4,615,696 | 10/1986 | Jackson .............................. 604/389 |
| 4,701,178 | 10/1987 | Glaug et al. ....................... 604/389 |
| 4,773,905 | 9/1988 | Moiee et al. . | |
| 4,834,820 | 5/1989 | Kondo ................................ 604/390 |
| 4,846,828 | 7/1989 | Mendelsohn ...................... 604/389 |
| 4,936,839 | 6/1990 | Molee et al. . | |

Primary Examiner—Paul J. Hirsch
Attorney, Agent, or Firm—Birch, Stewart, Kolasch & Birch

[57] ABSTRACT

In an absorbent article including a liquid permeable outer material, a liquid impermeable antileakage material, a liquid retentive absorbent element interposed therebetween, and a fixing device mounted on a back side of a generally vertically elongated absorbent article body and adapted to fix the body to a crotch portion of shorts, the fixing device has a pair of fixing elements, each of the fixing elements extending outwardly in a width direction from each lateral edge of the absorbent article body, the fixing element being provided on at least a back side thereof with an adhesive portion, the pair of fixing elements being able to be adhered to and separated from a back side of the absorbent article body through the adhesive portions.

6 Claims, 11 Drawing Sheets

SANITARY NAPKIN

BACKGROUND OF THE INVENTION

1. Field of the Invention

This invention relates to an absorbent article such as, catamenial napkin, incontinent pad, catamenial pad, etc. which a wearer wears together with an undergarment (hereinafter represented by "shorts") in the narrow crotch, and more particularly to an absorbent article having a high antileakage property.

2. Description of the Prior Art

The conventional absorbent article such as catamenial napkin basically includes a liquid permeable outer material, a liquid impermeable antileakage material, and a liquid retentive absorbent element interposed therebetween. In recent years, by developing and introducing a new material such as absorbent polymer as a material of an absorbent element besides the conventional cotton-like pulp or absorbent paper, it has been attempted to improve an absorption ability as an absorbent article. Another attempt has also been made in which a liquid permeable sheet, which is given a liquid permeability by forming tiny perforations on a hydrophobic sheet besides a non-woven fabric as a conventional fiber aggregate by various means, is used as an outer material in order to improve the absorption ability as an absorbent article.

However, even in an absorbent article in which a new material is introduced and in which each component element has an excellent efficiency, sideward leakage still occurs frequently in actual use. For example, in a case of catamenial napkins, blood leaks sidewardly by one cause or others and the blood reaches the shorts, which is apparently inconvenient phenomenon as a catamenial napkin and difficult to say that original efficiency of an absorbent article is fully exhibited. As main causes of leakage in a catamenial napkin occurrable irrespective of original efficiency of each component element, as mentioned above, the following three can be considered.

(1) When a wearer fixes a catamenial napkin on shorts, the position of the catamenial napkin is one-sided either rightward or leftward at the crotch portion of the shorts and there is a part, which is not covered with the catamenial napkin from the beginning, in the crotch portion.

(2) Even if a wearer successfully fixes a catamenial napkin in a generally right position, i.e., in a generally center area of the shorts without being one-sided either rightward or leftward relative to the crotch portion, the catamenial napkin is frequently twisted and deformed in a rolled-up state wherein each longitudinal edges of the catamenial napkin is overlapped with the central portion because of the wearer's physical activity or movements, and an edge portion of the crotch portion which was covered with the catamenial napkin is exposed due to the rolled-up deformation after it is worn.

(3) When a wearer moves hard, it is impossible to firmly fix a catamenial napkin to the crotch portion of a shorts only by fixing means such as adhesive which a catamenial napkin usually has, and the catamenial napkin is displaced from a predetermined position to expose the crotch portion.

Leakage caused by the above (1) through (3) is also greately affected by shorts to be worn by a wearer. For example, in case the width of the crotch portion, in particular, is wide compared with the width of the napkin, or in case fitness to the wearer's body is bad and loosened, leakage tends to occur comparatively easily.

Therefore, in order to solve these problems, many proposals were made in which an absorbent article is provided with a pair of flexible flaps each extending in the width direction away from a central portion of each longitudinal edge of the absorbent article (Japanese Patent Early Laid-open Publication Nos. Sho 60-75058 and Hei 1-111002). In the case of these absorbent articles, the crotch portion of the shorts, when in use, is sandwiched and fixed between the flaps in order to stabilize the absorbent article in the shorts, thereby improving the antileakage property.

For example, a sanitary napkin described in Japanese Patent Early Laid-open Publication No. Sho 60-75058 is designed such that in a central position of each vertical side of an absorbent article, a flexible flap formed of liquid permeable outer material and liquid impermeable antileakage material extends from each side of an absorbent element, so that the flap, in use, can be pulled out from the edge portion of the shorts and fixed to an outer side of the shorts by fixing and connecting means disposed on a rear surface of the flap, thereby stabilizing the sanitary napkin and improving the antileakage property. In this sanitary napkin, it is important, in order to have it exhibit its full antileakage property, to form an antileakage wall by placing the absorbent element in such a manner as that both sides of the absorbent element face upward when the shorts are worn. If the shorts are worn in such a state as just mentioned, leakage can be prevented to some extent. However, it gives rise to the following problems;

① Action for pulling out the flaps from both ends of the crotch of the shorts is not necessarily stable, the sanitary napkin cannot be worn together with the shorts in a constant state, and the sanitary napkin is sometimes twisted into an irregular form from the beginning of its use to cause leakage.

② If the width of the crotch portion of the shorts is wider than the width of the absorbent element, it becomes difficult to fix the sanitary napkin to the shorts or otherwise it sometimes happens that the sanitary napkin cannot be firmly secured to the crotch portion because an outwardlybent area of the crotch portion is reduced.

③ Even if the pair of flaps are firmly secured and the antileakage wall portion is successfully formed at each side of the absorbent element, it sometimes happens that the antileakage wall portion is twisted toward and contacted with the outer surface of the absorbent element to stain the flaps with blood. Therefore, although the stain of the shorts can be prevented by the flaps to some extent, it sometimes happens that even the flaps are stained while the wearer is moving or acting and the inner crotch portion is stained with blood by the stained flaps. This often renders even a greater damage to the wearer.

In any case, when the conventional absorbent articles described in the above-mentioned Publications are correctly fixed to a right position of shorts, leakage mentioned in the above (1) through (3) can be prevented to some extent, but in the case of shorts have a weak fitness to the wearer's body and a crotch portion which is wider in width than the width of an absorbent element, the flaps cover the outer surface of the absorbent article. As a result, leakage can not necessarily be prevented effectively and the flaps are stained which, in turn, stains the inner crotch portion with blood, etc.

SUMMARY OF THE INVENTION

An object of the present invention is to provide an absorbent article which can, easily and without fail, be fixed to undergarments such as shorts irrespective of the shape of the undergarments and fitness to a wearer's body, and which is hardly twisted even if the wearer performs physical activity, etc., and which can hold an initial wearing state stably from the beginning to the end of the use, and which can prevent leakage (particularly, sideward leakage) effectively.

Inventors of the present invention studied hard on absorbent articles which can, easily and without fail, be fixed to undergarments and particularly to shorts, etc. and which is capable of preventing sideward leakage effectively. As a result, they found that the above object can be achieved by employing certain fixing means.

The present invention has been made on a basis of the above finding and provides an absorbent article including a liquid permeable outer material, a liquid impermeable antileakage material, a liquid retentive absorbent element interposed therebetween, and a fixing device mounted on a back side of a generally vertically elongated absorbent article body and adapted to fix said body to a crotch portion of shorts, said fixing device having a pair of fixing elements, each of said fixing elements extending outwardly in a width direction from each lateral edge of said absorbent article body, said fixing element being provided on at least a back side thereof with an adhesive portion, said pair of fixing elements being able to be adhered to and separated from a back side of said absorbent article body through said adhesive portions ("first invention", when used hereinafter, refers to this invention).

According to the first invention, after, for example, the fixing elements of the fixing device are brought into abutted with an inner surface of a crotch portion of shorts in a state wherein the fixing elements of the fixing device are spread outside the absorbent article, the fixing elements are bent into their initial states and the adhesive portions are adhered to at least an outer surface of the crotch portion in such a manner as that both the lateral edges of the crotch portion are wrapped up with the fixing elements to fix the absorbent article to the shorts. If the shorts are worn in that state, the liquid permeable portion is located in a body fluids discharge portion and therefore, even if the wearer performs physical activity, etc. after the shorts are worn, the fixing elements are never tucked up, the crotch portion is normally wrapped up by the fixing elements in a state wherein the fixing elements are adhered to the crotch portion, and the absorbent article can be stably held in the initial wearing state from the beginning to the end of the use.

Also, the present invention provides an absorbent article having a liquid permeable outer material, a liquid impermeable antileakage material, and a liquid retentive absorbent element interposed therebetween, and formed in a generally vertically elongated shape, said absorbent article further including a fixing device mounted on a skin noncontacting surface side of said absorbent article and adapted to fix said absorbent article to shorts, said fixing device having a pair of fixing elements, each of said fixing elements having a free end which is located in an internal area of each longitudinal edge of said absorbent article ("second invention", when used hereinafter, refers to this invention).

According to the second invention, after, for example, the free ends of the fixing elements of the fixing device are brought into abutted with an inner surface of a crotch portion of shorts in a state wherein the free ends of the fixing device are spread outside the absorbent article, if the free ends are released, the free ends are returned to an inner side of the absorbent article from the outer surface of the crotch portion in such a manner as that the side edge portion of the crotch portion is wrapped up with the fixing device to fix the absorbent article to the shorts. If the shorts are worn in that state, the liquid permeable portion is located in a body fluids discharge portion and therefore, even if the wearer performs physical activity, etc. after the shorts are worn, the free ends are never tucked up, and the free ends are always located at an outer surface of the crotch portion, so that the absorbent article can be stably held in the initial wearing state from the beginning to the end of the use.

Accordingly, an absorbent article of the present invention can, easily and without fail, be fixed to undergarments such as shorts irrespective of the shape of the undergarments and fitness to a wearer's body, it is hardly twisted even if the wearer performs physical activity, etc., it can hold an initial wearing state stably from the beginning to the end of the use, and it can prevent leakage (particularly, sideward leakage) effectively. Furthermore, an absorbent article of the second invention can save separate paper and is economical.

DETAILED DESCRIPTION OF THE EMBODIMENT

Figure 1:
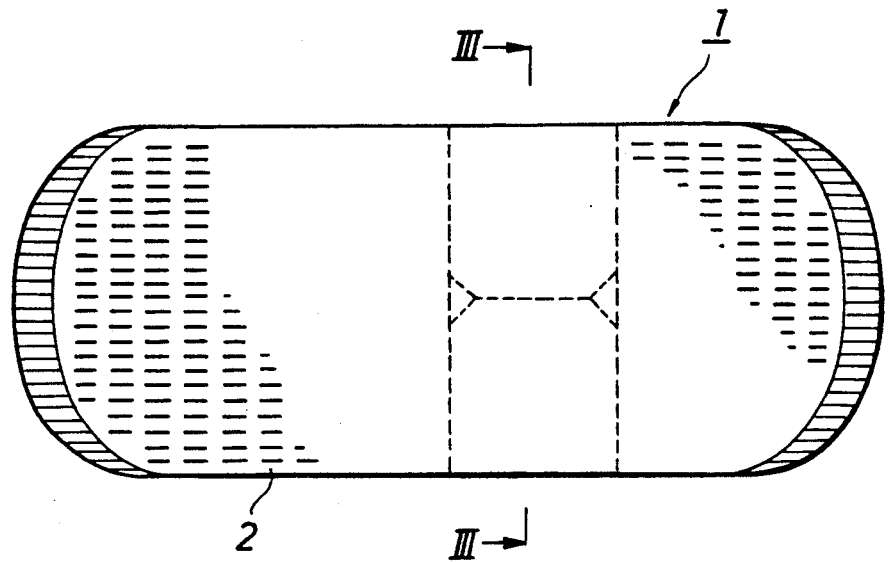
FIG. 1 is a plan view showing an outer surface side of a catamenial napkin as one embodiment of an absorbent article of the present invention.

The present invention (first invention) will be described hereinafter with reference to FIGS. 1 through 12.

A body of a catamenial napkin 1 of this embodiment, as shown in FIGS. 1 through 4, has a liquid permeable outer surface material (topsheet) 2 which is intended to contact with a wearer's skin, a liquid impermeable antileakage material (antileakage sheet) 3 which is intended to contact with shorts, a liquid retentive absorbent element 4 interposed between the sheets 2 and 3, and is formed in a generally vertically elongated shape. The topsheet 2 and antileakage sheet 3 may be integrally formed as shown in FIGS. 1 through 4. In this case, it may be designed, for example, such that the liquid impermeable sheet is provided with a plurality of tiny perforations, that part of the liquid impermeable sheet provided with the plurality of tiny perforations being located in a part of the topsheet 2, the remaining part having no tiny perforations being located in a part of the antileakage sheet 3. The catamenial napkin 1 is provided with a fixing device 7 adhered, by adhesive, etc., to the antileakage sheet 3 which is located on a skin non-contacting surface side of the catamenial napkin 1 and adapted to fix the catamenial napkin 1 to a crotch portion 6 of shorts 5 shown in FIGS. 5 and 6.

Figure 2:
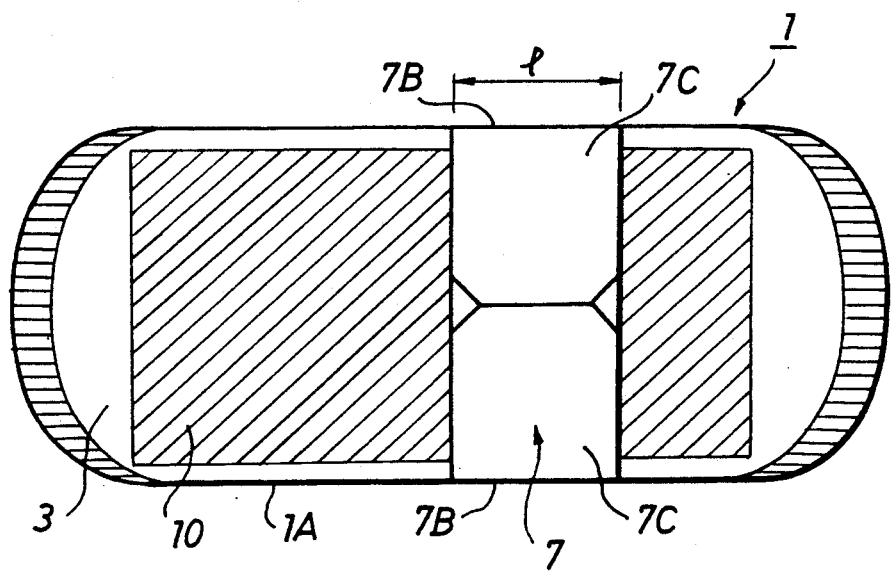
FIG. 2 is a plan view showing a lower surface side (back side) of the catamenial napkin of FIG. 1.

The fixing device 7, as shown in FIG. 2, is one-sided forwardly in the longitudinal direction of the catamenial napkin 1, and is longer than the width of the body of the catamenial napkin 1 when the fixing device 7 is expanded. The catamenial napkin 1 has an extended portion extending outwardly in the width direction from each longitudinal edge of thereof. The extended portions have free ends 7A, 7A which are bent inwardly so that the free ends 7A, 7A may be contacted with each other at the longitudinal center of the body of the catamenial napkin 1. The bent portions of the free ends 7A, 7A form a pair of side portions 7B, 7B, one having a horizontal U shape which is opened up at the righthand side and the other having likewise a horizontal U shape which is opened up at the left-hand side. The side portions 7B, 7B are formed along both longitudinal side portions 1A, 1A. Fixing elements (wing portions) 7C, 7C are formed by the afore-mentioned extended portions which are formed between the free ends 7A, 7A and the side portions 7B, 7B in such a manner as that the wing portions 7C, 7C can be bent at the side portions 7B, 7B.

Figure 3:
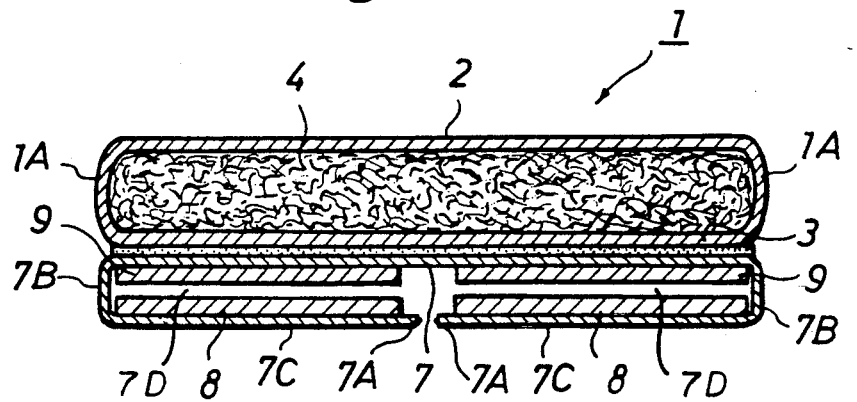
FIG. 3 is a sectional view taken on line III—III of the catamenial napkin of FIG. 1.

The fixing device (7), as shown in FIG. 3, is designed such that longitudinal edge portions 6A, 6A of the crotch portion 6 of the shorts 5 are held in spaces 7D, 7D between the wings 7C, 7C and the back side of the body of the catamenial napkin 1, so that the body of the catamenial napkin 1 is fixed to the crotch portion 6. Furthermore, the back side (side to be contacted with the shorts 5) of the wing portions 7C, 7C of the fixing device 7, and a surface of the body of the fixing device opposing those back sides are provided with adhesive portions 8, 9, respectively, so that the body of the catamenial napkin 1 is reliably fixed to the shorts 5 by adhering the fixing device 7 to the shorts 5 through the adhesive portions 8 and 9. The adhesive used in the adhesive portions 8 and 9 is of the type having a weak adhesive strength which requires no separate paper. One example of such adhesive is disclosed in Japanese Utility Model Early Laid-open Publication No. Sho 59-153304. Each of the adhesive portions 8 and 9 is provided on the fixing device 7 side with an adhesive having a strong adhesive strength and forming a lower layer, an adhesive having a weak adhesive strength being applied on the lower layer to form an upper layer, thereby forming a two-layer structure. By virtue of the two-layer structure of adhesives, the adhesive portions 8 and 9 can firmly be adhered to the fixing device 7. On the other hand, since the opposing adhesive portions 8 and 9 are adhered to each other with less amount of adhesive strength on the upper layer so that the mutually adhered adhesive portions 8 and 9 can easily be separated without using separate paper. As a result, the adhesive portions 8 and 9 can be adhered and separated with respect to each other. The strong adhesive is preferably of, for example, acrylic series or rubber series, while the weak adhesive is preferably of, for example, acrylic series. The adhesive strength of these adhesives can be adjusted properly by a well known method in the art. The afore-mentioned horizontal U shape, which is opened up either in the right-hand side or in the left-hand side may be ⊏ shape or ⊐ shape or any other suitable shapes. As long as the side portions 7B, 7B are folded back, the shapes of the respective portions are not particularly limited.

In the catamenial napkin 1 of this embodiment, an antislip portion 10 is formed over the generally entire surface of the antileakage sheet 3, so that it is not displaced in a state wherein the body of the catamenial napkin 1 is in contact with the shorts 5. The antislip portion 10 can be formed by applying, for example, a polymer having a glass transition temperature of 0° C. or less and a foamed expandable polymer beads which are described in Japanese Patent Early Laid-open Publication No. Sho 63-73959.

The outer sheet 2, antileakage sheet 3 and absorbent element 4 are preferably formed of known material which has been conventionally normally used.

Next, the mode of use of the catamenial napkin 1 will be described.

Figure 4:
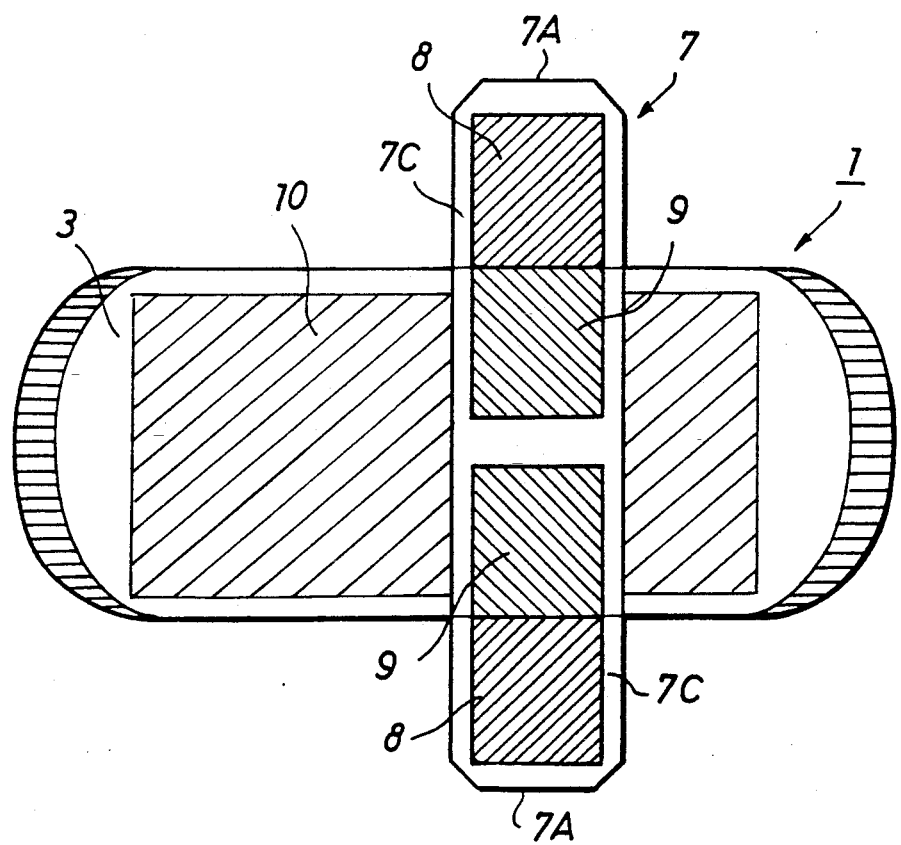
FIG. 4 is a plan view showing an expanded state of a fixing device of the catamenial napkin of FIG. 2.
Figure 5:
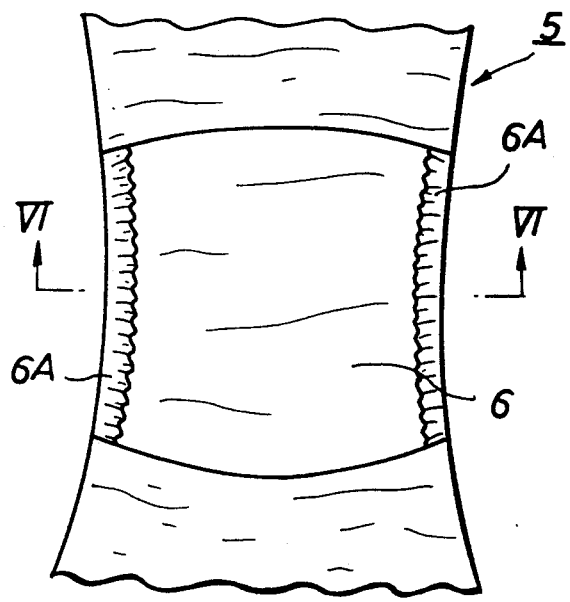
FIG. 5 is a plan view showing a crotch portion of shorts.
Figure 6:
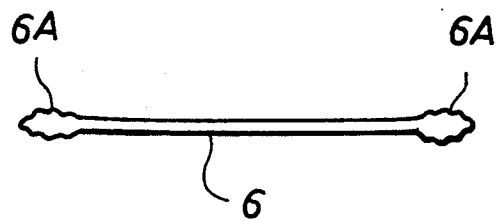
FIG. 6 is a sectional view of the crotch portion of FIG. 5.

To begin with, after each of the wing portions 7C, 7C of the fixing device 7 is separated from the body of the catamenial napkin 1 which is in the state as shown in FIG. 2 and makes it in an expanded state as shown in FIG. 4 wherein the wing portions 7C, 7C are spread outside the body of the catamenial napkin 1, the catamenial napkin 1 is brought into abutment with the crotch portion 6 of the shorts 5 shown in FIGS. 5 and 6, and fixed to the crotch portion 6 through the adhesive portions 9, 9 of the body of the fixing device 7. Then, when the pair of wing portions 7C, 7C are bent inwardly from both edge portions 6A, 6B to wrap up the crotch portion 6, the adhesive portions 8, 8 of the wing portions 7C, 7C are adhered to the outer surface of the crotch portion 6, thereby fixing the catamenial napkin 1 to the crotch portion 6. If the shorts 5 with the catamenial napkin 1 adhered thereto in the manner as just mentioned are worn by a wearer, the catamenial napkin 1, while holding the state wherein it is fixed by the fixing device 7, is intimately attached to the crotch portion of the wearer depending on the shape of the wearer's crotch.

Therefore, according to this embodiment, since the respective wing portions 7, 7 are merely adhered to each other with a weak strength through the adhesive portions 8 and 9, when the catamenial napkin 1 is fixed, if the wing portions 7C, 7C are pulled out from the edge portions 6A, 6A of the crotch portion 6 by easily spreading the wing portions 7C, 7C and adhered to the inner surface of the crotch portion 6 with the adhesive portions 9, 9 of the fixing device 7 and then the wing portions 7C, 7C are bent toward the outer surface face of the crotch portion 6, they are adhered to the outer surface of the crotch portion 6 with the adhesive portions 8, 8, thereby fixing the catamenial napkin 1 to the crotch portion 6. Accordingly, the fixing operation is very convenient and no fixing error will occur. Further, after the shorts are worn, accompanying with the function of the antislip portion 10, the body of the catamenial napkin 1 can be reliably fixed to the crotch portion 6 by the two pairs of adhesive portions 8 and 9. Moreover, the catamenial napkin 1 is not displaced and held stable in its initially fixed state. Even if the shape of the crotch portion is greatly changed due to the wearer's physical activity or movements, the body of the catamenial napkin 1 is never displaced by following the changes, thus enabling to prevent the catamenial napkin 1 from being twisted. As a result, there is no fear that the shorts 5 and inner crotch portion are stained with blood. Furthermore, according to this embodiment, since the adhesive portions 8 and 9 require no separate paper, expensive separate paper can be saved and therefore, an economical catamenial napkin 1 can be obtained.

The absorbent article of the present invention can be constructed as catamenial napkins 1 which are shown in FIGS. 7 through 12, respectively.

Figure 7:
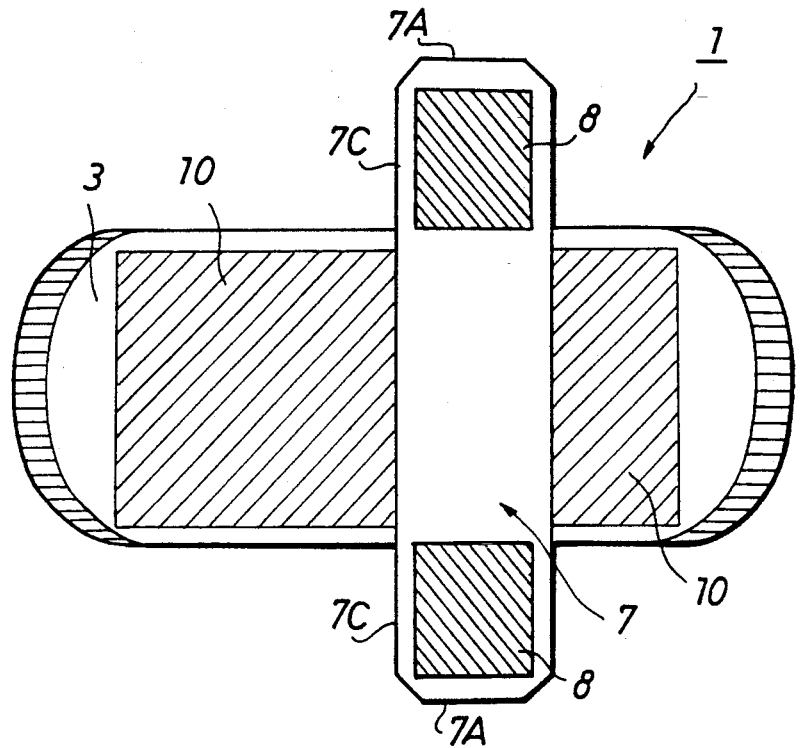
FIGS. 7 and 8 are views corresponding to FIG. 4, showing a catamenial napkin as another embodiment of an absorbent article of the present invention.
Figure 8:
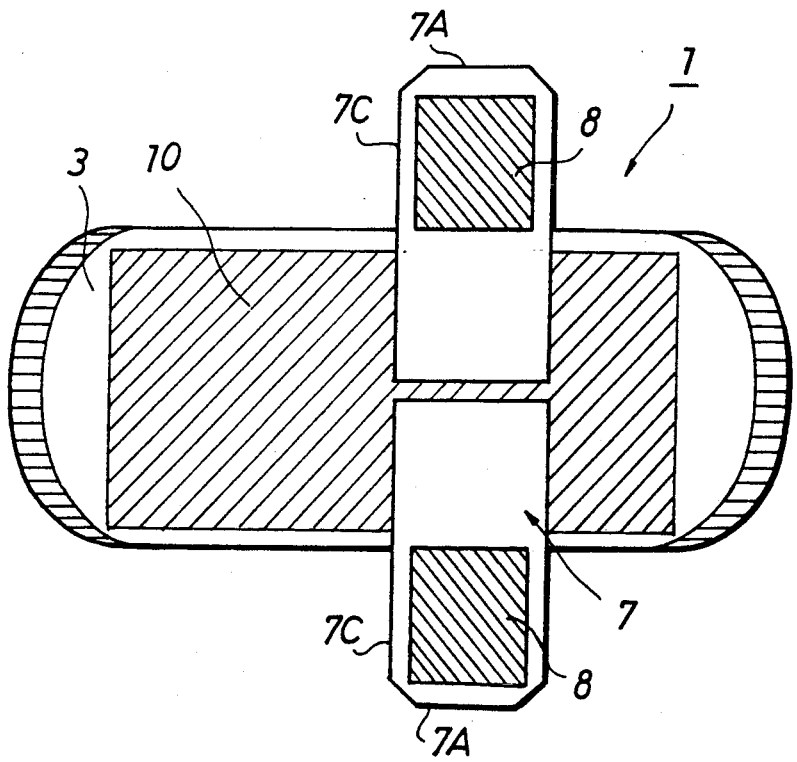

The catamenial napkin 1 shown in FIG. 7 is constructed, as shown in said Figure, in the same manner as the above-mentioned embodiment except that adhesive portions 9, 9 of the body of the afore-mentioned catamenial napkin 1 are omitted. Similarly, the catamenial napkin 1 shown in FIG. 8 is constructed in the same manner as the catamenial napkin 1 shown in FIG. 7 except that the fixing device 7 shown in FIG. 7 is divided into two at the center in the width direction. According to these embodiments, besides there can be expected the similar function and effect as in the above-mentioned embodiment, the adhesive portions 9, 9 of the body of the fixing device 7 of the catamenial napkin 1 shown in FIGS. 1 through 4 can be save.

Figure 9:
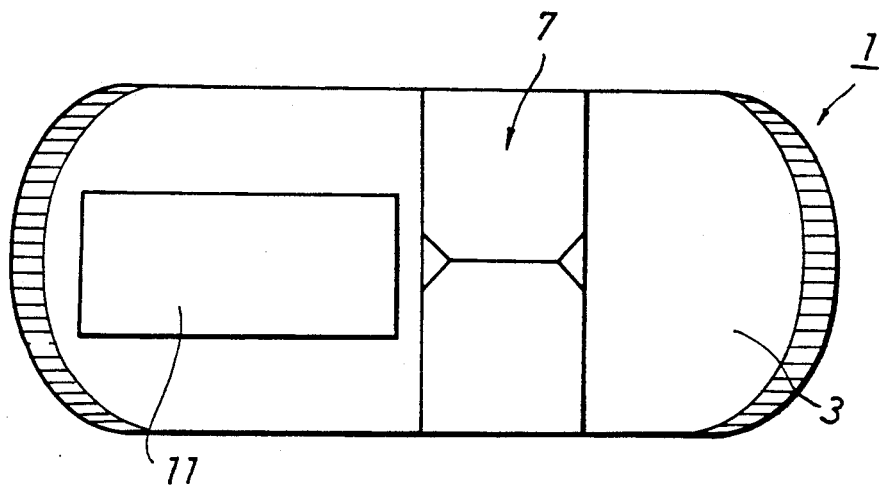
FIG. 9 is a view corresponding to FIG. 2, showing a catamenial napkin as a further embodiment of an absorbent article of the present invention.
Figure 10:
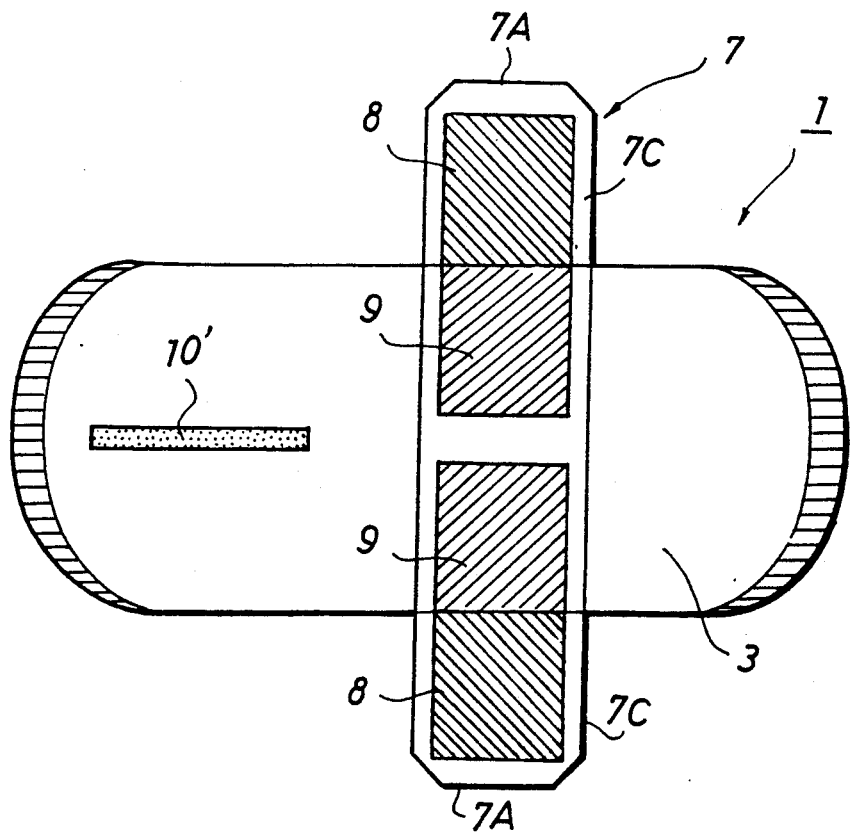
FIG. 10 is a view corresponding to FIG. 9, showing the catamenial napkin of FIG. 9.

Likewise, the catamenial napkin 1 shown in FIGS. 9 and 10 is constructed in the same manner as the catamenial napkin 1 shown in FIGS. 1 through 4 except that instead of the antislip portion 10 disposed over the generally entire surface of the antileakage sheet 3 in the catamenial napkin 1 shown in FIGS. 1 through 4, adhesive is applied to a generally central area behind the antileakage sheet 3 to form an adhesive portion 10' and a separate paper 11 is attached to the adhesive portion 10'. The similar function and effect as in the above-mentioned embodiments can be expected in this embodiment, too.

Figure 11:
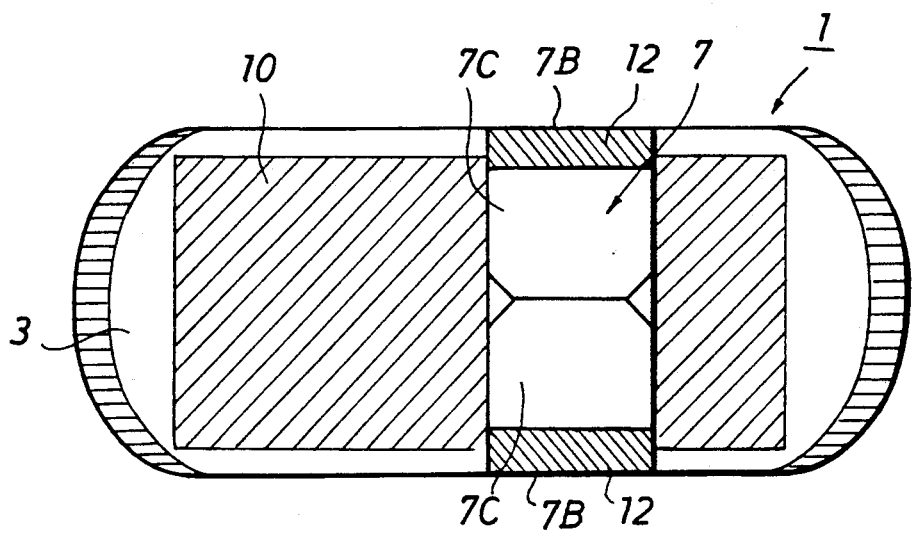
FIG. 11 is a view corresponding to FIG. 2, showing a catamenial napkin as a still further embodiment of an absorbent article of the present invention.
Figure 12:
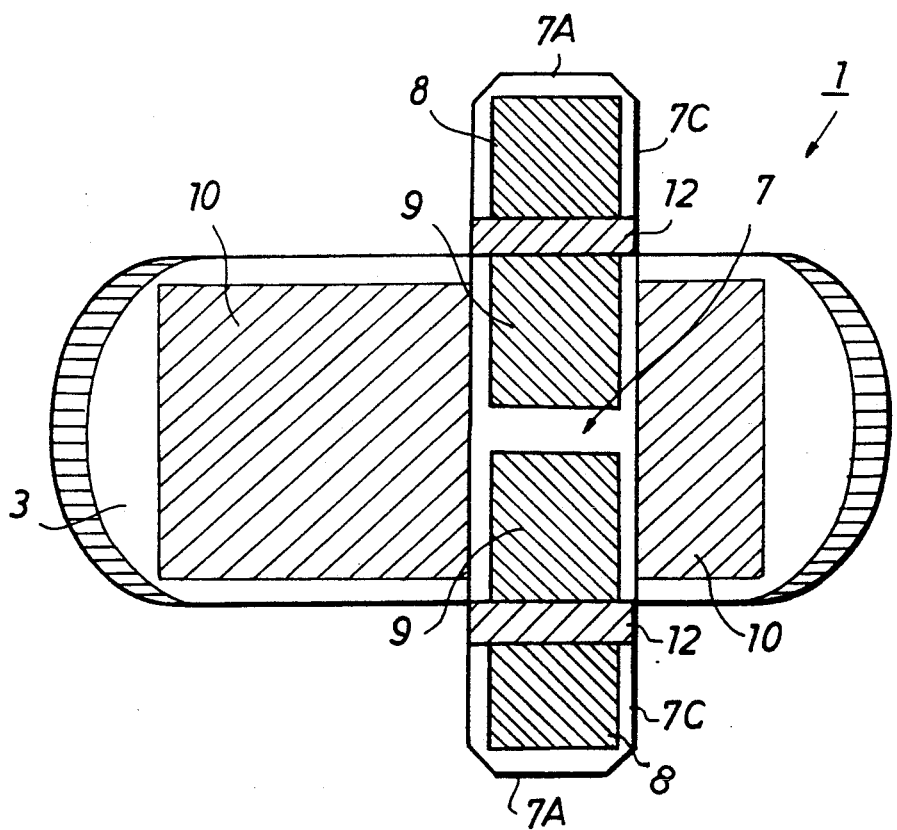
FIG. 12 is a view corresponding to FIG. 4, showing the catamenial napkin of FIG. 11.

Similarly, the catamenial napkin 1 shown in FIGS. 11 and 12 is constructed in the same manner as in the catamenial napkin 1 shown in FIGS. 1 through 4 except that as shown in said Figures, expansible elastic members 12, 12 are disposed to the side portions 7B, 7B of the fixing device 7 shown in FIGS. 1 through 4. According to this embodiment, the expansible members 12, 12 of the fixing device 7 follow the radical change of the crotch portions 6A, 6A in accordance with the wearer's physical activity or movements when the catamenial napkin 1 is worn, and loads incurred to the adhesive portions 8 and 9 are absorbed and reduced by expansion and construction of the elastic members 12, 12, thus enabling to more stabilize the fixing state of the catamenial napkin 1.

The absorbent article of the present invention is not limited to the fixing device of the above-mentioned embodiments as long as a pair of fixing elements extending outwardly in the width direction are connected to both longitudinal edges of the body of the absorbent article, an adhesive portion is disposed to at least on a back side of each of the pair of fixing elements, and the pair of fixing elements can be adhered to and separated from the fixing element on the back side of the body of the absorbent article through the adhesive portions. For example, it may be designed such that free ends of the fixing elements are bent in order to facilitate an easy pull-out.

Furthermore, the fixing element of the present invention may also be designed such that by non-elastically deforming the edge portions 7B, 7B, a bending habit (stress) for naturally folding the free ends 7A, 7A inwardly is applied so that the wing portions 7C, 7C can normally be held on the back side of the body of the catamenial napkin.

Next, the present invention (second invention) will be described with reference to the embodiment shown in FIGS. 13 through 16.

Figure 13:
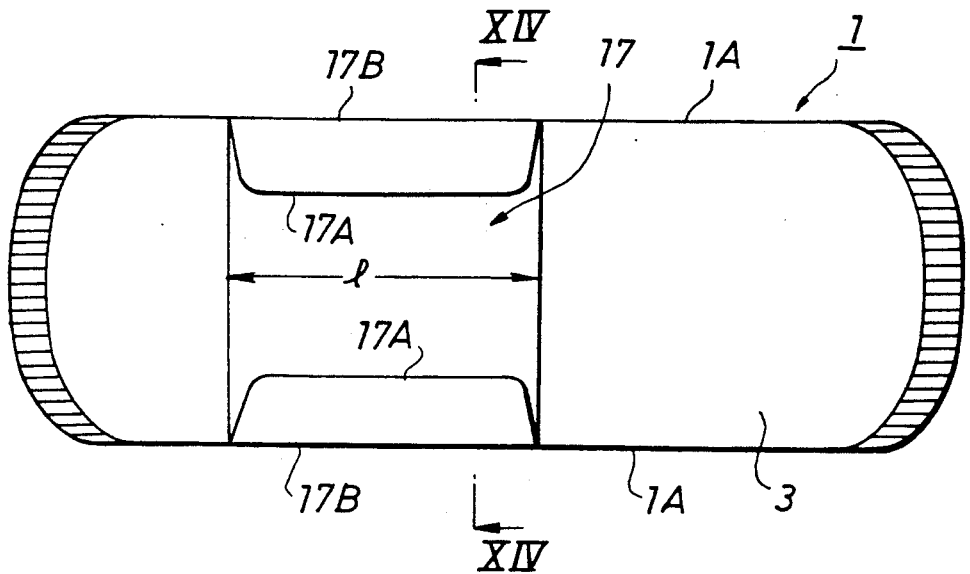
FIG. 13 is a plan view showing a back side of a front surface side of the catamenial napkin as one embodiment of the present invention.
Figure 14:
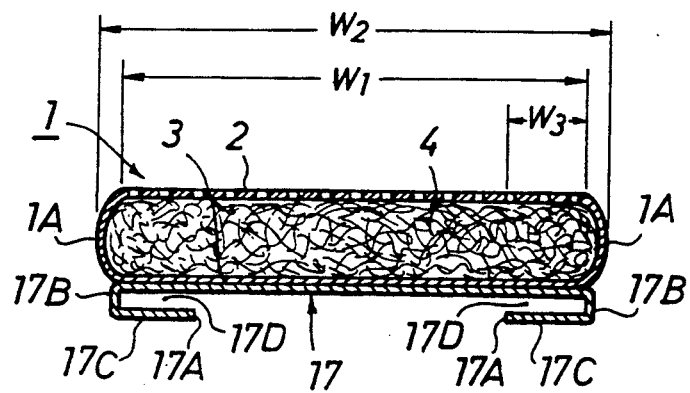
FIG. 14 is a sectional view taken on line X—X of FIG. 13.

A catamenial napkin 1 of this embodiment, as shown in FIGS. 13 and 14, has a liquid permeable outer surface material (topsheet) 2 which is intended to contact with a wearer's skin, a liquid impermeable antileakage material (antileakage sheet) 3 which is intended to contact with shorts, a liquid retentive absorbent element 4 interposed between the sheets 2 and 3, and is formed in a generally vertically elongated shape. The topsheet 2 and antileakage sheet 3 may be integrally formed as shown in afore-mentioned Figures. In this case, it may be designed, for example, such that the liquid impermeable sheet is provided with a plurality of tiny perforations, that part of the liquid impermeable sheet provided with the plurality of tiny perforations being located in a part of the topsheet 2, the remaining part having no tiny perforations being located in a part of the antileakage sheet 3.

In this embodiment, the antileakage sheet 3, which is located on a skin non-contacting surface side of the catamenial napkin 1 is provided with a fixing device 17 adapted to fix the catamenial napkin 1 to a crotch portion 6 of shorts 5 shown in FIGS. 5 and 6. The fixing device 17, as shown in FIG. 13, is one-sided forwardly in the longitudinal direction of the catamenial napkin 1. Furthermore, the fixing device 17 has a pair of fixing elements 17C, 17C, and both free ends 17A, 17A in the longitudinal direction are bent to exhibit a horizontal U shape which is opened up at the right-hand side and a horizontal U shape which is opened up at the left-hand side, so that both free ends 17A, 17A are located inside the catamenial napkin 1, respectively. The bent portions form side portions 17B, 17B which are generally coincident with both side portions 1A, 1A in the longitudinal direction of the catamenial napkin 1. That is, in the fixing device 17, the pair of right and left free ends 17A, 17A are located inside the both side portions 1A, 1A, and the fixing elements 17C, 17C are formed between the free ends 17A, 17A and both side portions 17B, 17B. The fixing device 17 has spaces 17D, 17D between the fixing elements 17C, 17C and the back side of the body of the catamenial napkin 1, the spaces 17D, 17D adapted to allow both edges 6A, 6A of the crotch portion 6 of the shorts 5 to be interposed therein, thereby fixing the catamenial napkin 1 to the crotch portion 6.

The afore-mentioned horizontal U shape which is opened up either in the right-hand side or in the left-hand side may be ⊂ shape or ⊐ shape or any other suitable shapes. As long as the side portions 17B, 17B are folded back, the shapes of the respective portions are not particularly limited.

The length l of the fixing device 17 is preferably set to 20 to 120 mm taking into consideration the fixing function in the space 17D, material of the fixing device 17, or balancing with moldability of the bent portion, and more preferably 50 to 100 mm. Although a connecting and fixing width $w_1$ of the fixing device 17 with respect to the catamenial napkin 1 is not particularly limited, it suffices as long as there is no significant difference with respect to the width of the body of the catamenial napkin 1. Normally, a difference between the connecting and fixing width $w_1$ and the width $w_2$ of the body of the catamenial napkin 1 is preferably as follows;

$$|w_1 - w_2| < 10$$

Since, for example, the width of the catamenial napkin 1 is, in general, 60 to 80 mm, the width $w_1$ of the fixing device 17 is preferably 50 to 90 mm.

Although the width $w_3$ of the fixing element 17C is not particularly limited, it is preferably set to 10 to 20 mm taking into consideration an easy fixture of the catamenial napkin 1 to the crotch portion 6. In the crotch portion 6 of the shorts 5, both edges 6A, 6A are trimmed with an expansible rubber, lace or the like and therefore, have some thickness.

The side portions 17B, 17B have stress for naturally positioning the free ends 17A, 17A inside, and also have a bending habit by plastic deformation so that the respective fixing elements 17C, 17C can normally be held on the back side of the body of the catamenial napkin 1. Therefore, the fixing device 17 has such a shape maintaining ability as that when the free end 17A is grasphed by hand and separated from the body of the catamenial napkin 1 in order to release the fixing device 17, the free end 17A is swung toward the back side of the body of the catamenial napkin 1 so as to be returned to its initial state.

Figure 17:
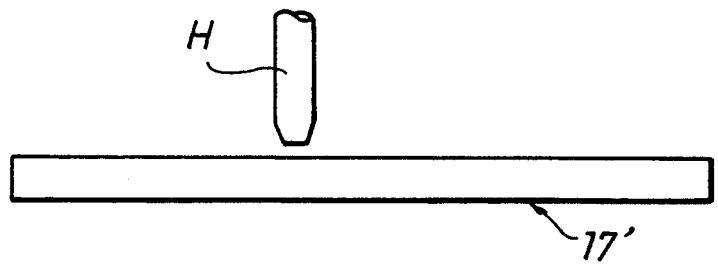
FIGS. 17, 18 and 19 are explanatory views showing each step for forming a fixing device, respectively.
Figure 18:
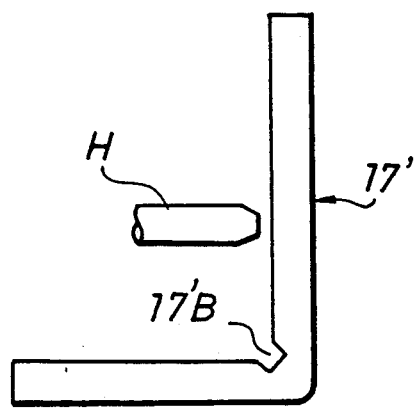
Figure 19:
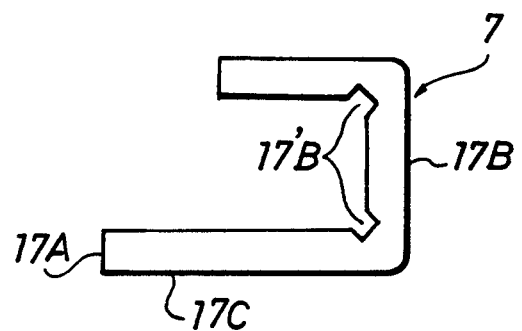

Next, one example of a method for molding the fixing device 17 will be briefly described with reference to FIGS. 17 through 19. First, a sheet material formed of a polyolefin-series foam body, a polyurethane series foam body or the like is cut into a predetermined size to make a sheet 17'. Then, a heating medium H is pushed against a predetermined position of the sheet 17', as shown in FIG. 17, thereby contracting a heating portion 17'B of the sheet 17' by heating in order to fold the sheet 17' by 90° as shown in FIG. 18. Furthermore, the heating medium H is pushed against an area next to the heating portion 17'B, thereby contracting the heating portion 17'B by heating in order to fold the sheet 17' by 90°, as shown in FIG. 19, to mold the fixing device 7. Such molded folding-back portion is served as the side portion 17B in the fixing device 17. An end of the expanded portion, which is not fixed to the body of the catamenial napkin 1, is served as the free end 17A, and the expanded portion is served as the fixing element 17C. The fixing device 17 of this embodiment is obtained by integrally forming the folding-back portions which are located in right and left positions as shown in FIG. 19. If the sheet 17' is heated by a heating medium H having a higher temperature, it can be folded back by 180° at a time.

Although material used for the fixing device 17 is not particularly limited, such material is preferably either a simple substance or a mixture of polyethylene, polypropylene, polyvinyl chloride, ionomer resin and modified resin thereof. A form for processing such material as just mentioned is preferably a film (single layer or multi-layer), an independent foam sheet, a communicating foam sheet or the like.

The topsheet 2, backsheet 3 and absorbent element 4 is preferably formed of a known material which has heretofore normally used.

Next, a mode for using the catamenial napkin 1 will be described.

Figure 15:
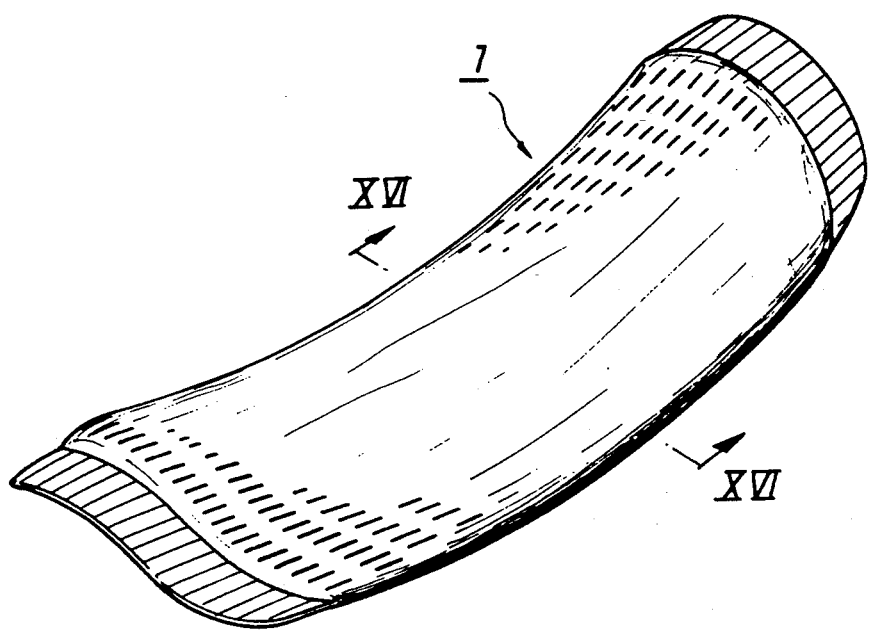
FIG. 15 is a perspective view showing a form of the catamenial napkin of FIG. 13 when in use.
Figure 16:
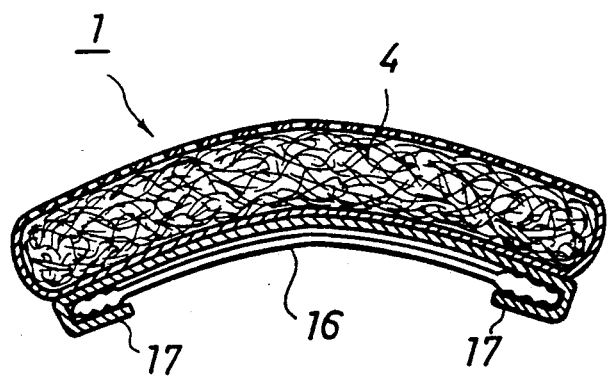
FIG. 16 is a sectional view taken on line Y—Y of FIG. 15.

First, the respective fixing elements 17C, 17C of the fixing device 17 are held in a state wherein the fixing elements 17C, 17C are spread outwardly from the body of the catamenial napkin 1, and the catamenial napkin 1 is brought into abutment with the crotch portion 6 of the shorts 5. Then, when the respective fixing elements 17C, 17C are released, they are naturally returned to their initial states by stress acting on the side portions 17A, 17A and caused to wrap up both edges 6A, 6A of the crotch portion 6 therein, thereby fixing the catamenial napkin 1 to the crotch portion 6. Thereafter, when the wearer wears the shorts 5 and the crotch portion 6 is pushed against the wearer's crotch portion, the catamenial napkin 1 is deformed into a saddle shape following the shape of the wearer's crotch portion as shown in FIG. 15. At that time, force for tightening the wearer's body acts in the direction as shown by an arrow of FIG. 16 from each edge 6A, 6A of the crotch portion 6. As a result, the both curved side portions 1A, 1A of the catamenial napkin 1, and the areas slightly inner side of the both side portions 17B, 17B of the fixing device 17 are pushed against the wearer's crotch portion, thereby reliably fixing the catamenial napkin 1 to the shorts 5.

Therefore, according to this embodiment, irrespective of the size of the shorts 5, the catamenial napkin 1 can be fixed to the crotch portion 6 by easily and reliably pulling out the fixing elements 17C, 17C from both edges 6A, 6A of the crotch portion 6 in the shorts 5, and after the shorts 5 are worn, the areas slightly inner side of both side portions 1A, 1A of the catamenial napkin 1 are reliably pushed against the wearer's crotch portion by both edges 6A, 6A of the crotch portion 6 to stabilize the using state of the catamenial napkin 1. As a result, the catamenial napkin 1 can be prevented from being twisted.

Furthermore, according to this embodiment, since the fixing device 17 is located on the back side of the body of the catamenial napkin 1 and the fixing elements 17C, 17C are normally in contact with the outer surface of the crotch portion 6 so as to be readily deformed in accordance with the shape of the wearer's crotch portion, even if the shape of the wearer's crotch portion is radically changed due to the wearer's physical activity or movements, it never happens that the catamenial napkin 1 is displaced to twist the fixing elements 17C, 17C toward the front surface side and the fixing elements 17C, 17C are stained with blood. Therefore, there is no fear that the wearer's crotch portion is stained with blood, too.

FIGS. 20, 21, 22 and 23 are sectional views respectively showing a catamenial napkin as another embodiment of the absorbent article of the present invention. Since the catamenial napkins 1 of these embodiments are constructed in the same manner as the above-mentioned embodiment excepting the sectional configuration of the fixing device 17, only fixing devices 17 will be described.

Figure 20:
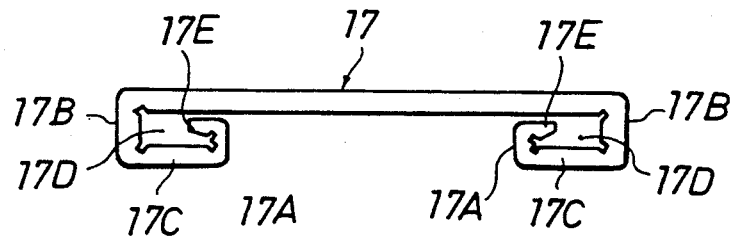
FIGS. 20, 21, 22 and 23 are views corresponding to FIG. 14, showing yet further embodiments of the present invention, respectively.

The fixing device 17 shown in FIG. 20 is designed such that a pair of free ends 17A, 17A are folded back toward the side portions 17B, 17B side, and fold-back stepped portions 17E, 17E are disposed within spaces 17D, 17D. Since there are the fold-back stepped portions 17E, 17E within the spaces 17D, 17D, rigidity is given to each free end 17A, 17A. In addition, since the fold-back stepped portions 17E, 17E are retained by the thick wall portions of both edges 6A, 6A in the crotch portion 6 to increase the resistance of the fixing elements 17C, 17C, a more reliable fixing function of the fixing device 17 can be obtained.

Figure 21:
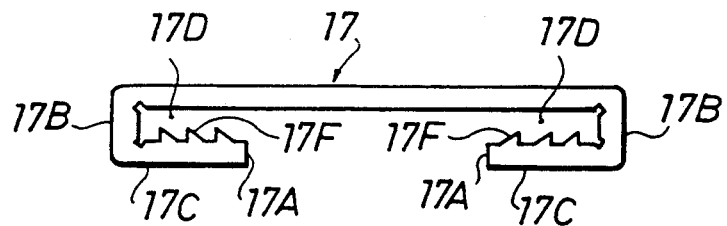

In the fixing device 17 shown in FIG. 21, instead of the fold-back stepped portions 17E, 17E in the fixing device 17 shown in FIG. 20, a plurality of projections 17F, 17F are formed on the surfaces on the spaces 17D, 17D side in the fixing elements 17C, 17C, so that the resistance of the fixing elements 17C, 17C with respect to the crotch portion 6 is increased.

Figure 22:
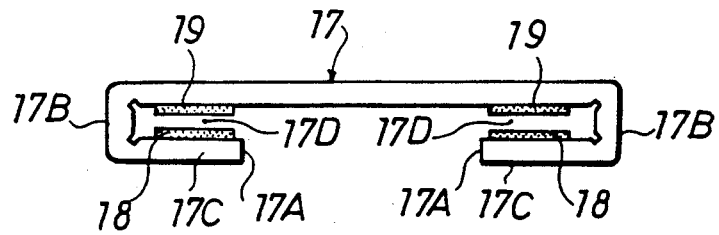

In the fixing device 17 shown in FIG. 22, the fixing elements 17C, 17C are provided with adhesive portions 18, 19 on a surface on the spaces 17D, 17D side and a surface opposed thereto, respectively, in order to more ensure the fixing function of the fixing device 17 by virtue of the provision of the adhesive portions 18 and 19. Adhesive used in the adhesive portions 18 and 19 is preferably of the type having a weak adhesive strength which requires no separate paper. One example of such adhesive is described in Japanese Utility Model Early Laid-open Publication No. Sho 59-153304. Furthermore, by constructing each of the adhesive portions 18 and 19 in a two-layer structure, i.e., by constructing each of the adhesive portions 18 and 19 in such a two-layer structure as that an adhesive having a strong adhesive strength is applied to the fixing device 7 side so as to be served as a lower layer and an adhesive having a weak adhesive strength is applied thereon so as to be served as an upper layer, the adhesive portions 18 and 19 are firmly adhered to the fixing device 17 and when not in use, even if the opposing adhesive portions 18 and 19 are adhered to each other in the upper layer, they can easily be separated and no separate paper is required to be used. Also, the adhesive may be applied to only the fixing element 7C, or it may also be applied to a surface facing with the projection 17F of the fixing element 17C in the fixing device 17 shown in FIG. 21.

The strong adhesive is preferably selected from, for example, acrylic series or rubber series, while the weak adhesive is preferably selected from, for example, acrylic series.

Figure 23:
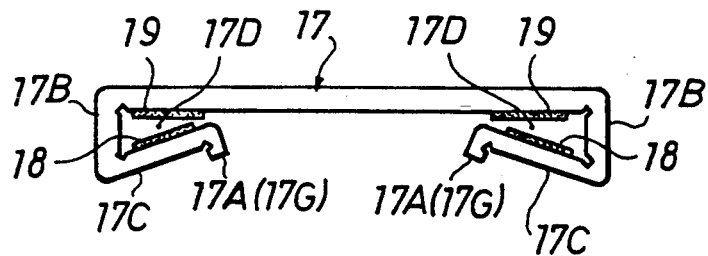

The fixing device 17 shown in FIG. 23 is constructed in the same manner as the fixing device 17 shown in FIG. 22 except that each free end 17A, 17A is folded back toward the other side of the spaces 17D, 17D, each end of the foldedback portions is served as a handle portion 17G, 17G, each free end 17A, 17A is approached to the body side, and each fixing element 17C, 17C is inclined. In the fixing device 17, even if the adhesive portions 18 and 19 are adhered to each other, the fixing element 17C can easily be separated and spread by properly handling the handle portion 17G.

In the above-mentioned fixing devices 17, the side portions 17B, 17B may be curved in accordance with the configurations of both edges 6A, 6A of the crotch portion 6.

Figure 24:
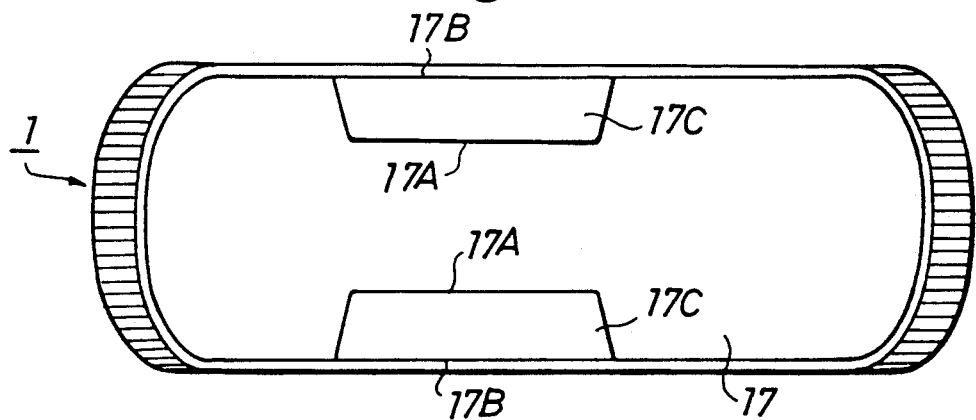
FIG. 24 is a plan view showing a back side of a catamenial napkin as an additional embodiment of an absorbent article of the present invention.
Figure 25:
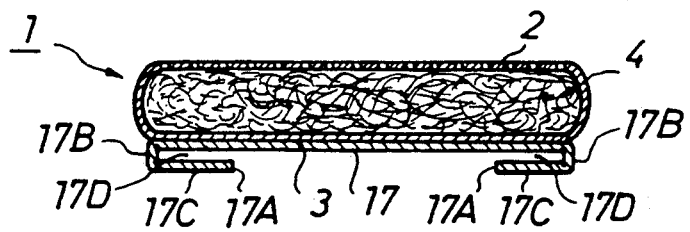
FIG. 25 is a sectional view showing an important portion of FIG. 24.

FIGS. 24 and 25 are views respectively showing a catamenial napkin 1 according to an additional embodiment of the present invention (second invention). The catamenial napkin 1 of this embodiment is constructed in the same manner as the above-mentioned respective embodiments except that, as shown in the afore-mentioned Figures, the fixing device 17 exhibits a plane configuration formed on a basis of the back of the catamenial napkin 1, i.e., antileakage sheet 3, the entire surface of the antileakage sheet 3 is covered with the fixing device 17, and a pair of fixing elements 17C, 17C are disposed to position one-sided forwardly in the longitudinal direction of the fixing device 17.

Figure 26:
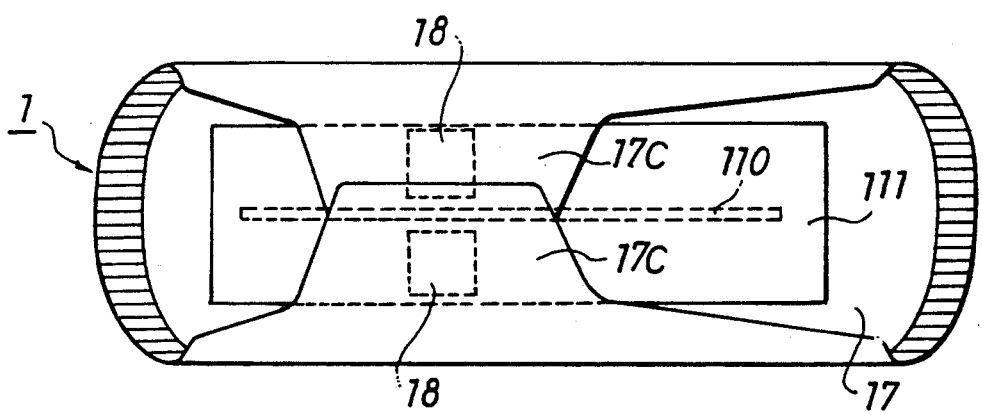
FIGS. 26 and 27 are views corresponding to FIGS. 24 and 25, showing still additional embodiments of an absorbent article of the present invention, respectively.
Figure 27:
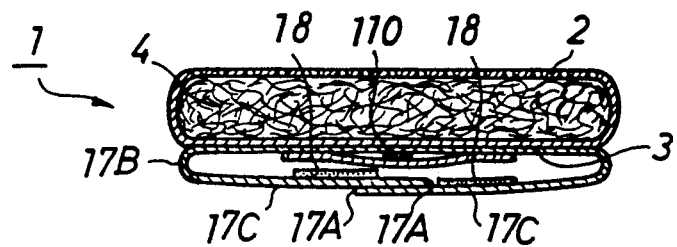

FIGS. 26 and 27 are views showing respectively a catamenial napkin 1 according to a still additional embodiment of the present invention (second invention). In the catamenial napkin 1 of this embodiment, as shown in the afore-mentioned Figures, the free ends 17A, 17A of a pair of fixing elements 17C, 17C in the fixing device 17 are overlapped with each other, and the adhesive portions 18, 18 are disposed to inside the fixing elements 17C, 17C. A pulselike adhesive portion 110 is disposed to the center in the longitudinal direction of the body of the fixing device 17, so that it can be fixed to the crotch portion 6 of the shorts 5 together with the afore-mentioned adhesive portion 18. Only excepting the foregoing construction, the catamenial napkin 1 of this embodiment is constructed in the same manner as the catamenial napkin 1 shown in FIGS. 24 and 25.

Accordingly, also in each embodiment shown in FIGS. 24 through 27, the similar function and effect as in the embodiments shown in FIGS. 13 and 14 can be expected.

Although description was made only on a fixing device 17 in which a pair of fixing elements 17C, 17C are integrally formed together in the above-mentioned embodiments, a fixing device in the present invention may be designed such that as shown in FIGS. 19, the fixing elements 17C, 17C are independent. In a case of such independent fixing device, it goes without saying that a separate fixing device may be provided to each side portion of the catamenial napkin 1.

An absorbent article of the present invention is likewise applicable to an absorbent article for the use in incontinent pads, catamenial pads, etc. besides the catamenial napkins in the above-mentioned embodiments.

What is claimed is:

1. An absorbent article having a body with generally vertically elongated sides, comprising:
    a liquid permeable outer material top layer to be located next to a wearer's body;
    a liquid impermeable antileakage material bottom layer to be located next to a wearer's shorts;
    a liquid retentive absorbent element interposed between said top layer and said bottom layer; and a fixing device mounted on said bottom layer and adapted to fix said body to a crotch portion of the wearer's shorts;

said fixing device comprising an antislip portion formed over generally an entire surface of said bottom layer, and a pair of fixing elements mounted on a section of said bottom layer;

said fixing elements having a first surface in contact with said bottom layer and a second surface having adhesive portions thereon, said adhesive portions comprising a two-layer adhesive structure having a first layer of strong adhesive strength applied to said second surface of the fixing elements, and a second layer of weak adhesive strength applied to said first layer; said second layer being easily releasable from itself;

said fixing elements being foldable so as to remain within said vertically elongated sides of the body, and said fixing elements being unfoldable so as to extend outwardly from said vertically elongated sides of the body;

said adhesive portion and said antislip portion requiring no release paper.

2. The absorbent article of claim 1, wherein said adhesive portions are present on said second surface of the fixing elements only in an area of said fixing elements which extends outwardly from said vertically elongated sides of the body in an unfolded state.

3. The absorbent article of claim 1, wherein said adhesive portions are present on generally the entire second surface of the fixing elements such that said adhesive portions adhere to one another in a folded state and separate from one another in an unfolded state.

4. The absorbent article of claim 1, wherein said fixing elements comprise one continuous strip of material.

5. The absorbent article of claim 1, wherein said fixing elements comprise two separate pieces of material.

6. The absorbent article of claim 1, wherein said fixing elements include expansible members located in an area of said fixing elements which is located adjacent to and outboard of said vertically elongated sides when said fixing elements are in an unfolded state.

* * * * *